United States Patent [19]

Studt et al.

[11] Patent Number: 4,544,670

[45] Date of Patent: Oct. 1, 1985

[54] METHOD OF TREATING COCCIDIOSIS WITH ACYL GUANIDINES

[75] Inventors: William L. Studt, Harleysville; Stuart A. Dodson, Lansdale; Harry K. Zimmerman, Kintnersville; James L. Barnes, Glenside, all of Pa.

[73] Assignee: William H. Rorer, Inc., Fort Washington, Pa.

[21] Appl. No.: 410,958

[22] Filed: Aug. 24, 1982

[51] Int. Cl.$^4$ .................. A01N 33/02; A01N 37/30
[52] U.S. Cl. ........................... 514/617; 514/622
[58] Field of Search ............ 424/316, 330; 564/182; 548/352; 514/617, 622

[56] References Cited

U.S. PATENT DOCUMENTS

| | | | |
|---|---|---|---|
| 2,734,904 | 2/1956 | Burtner | 564/170 X |
| 2,740,815 | 4/1956 | Feichtinger et al. | 564/90 |
| 3,608,087 | 9/1971 | Patchett et al. | 564/90 X |
| 3,632,645 | 1/1972 | Bream et al. | 564/182 X |
| 3,828,078 | 8/1974 | Mrozik | 564/86 X |
| 4,318,915 | 3/1982 | Cohnen et al. | 564/182 X |
| 4,340,609 | 7/1982 | Chou | 424/322 |

OTHER PUBLICATIONS

Burger, "Medicinal Chemistry", 3rd Ed., Part I, pp. 570–571, (1970).

*Primary Examiner*—Robert V. Hines
*Attorney, Agent, or Firm*—James A. Nicholson; Alexis Barron; Martin F. Savitzky

[57] ABSTRACT

Methods for the treatment of physiological disorders, including protozoal infections in mammalian and avian species and gastrointestinal and cardiovascular disorders in mammalian species by administering a class of aralkyl- and aralkenyl-acyl, and thioacyl, guanidine compounds, pharmaceutical compositions containing such compounds for systemic administration, and a class of novel aralkenyl-, aryl-substituted cycloalkyl-, and arylsubstituted heterocycle-acyl and thioacyl guanidines.

5 Claims, No Drawings

METHOD OF TREATING COCCIDIOSIS WITH ACYL GUANIDINES

FIELD OF THE INVENTION

This invention relates to aralkyl- and aralkenyl-acyl, and thioacyl, guanidines and to their use in treating mammalian and avian species afflicted with protozoal infections or with gastrointestinal or cardiovascular disorders.

REPORTED DEVELOPMENTS

Amidines and related compounds, such as guanidines and amidinoureas, are known to exhibit certain physiological activity in mammalian species, including antihypertensive action. Exemplary antihypertensive aralkylacetylguanidines are disclosed in U.S. Pat. Nos: 3,632,645; 3,634,508; 3,822,262; and, 4,318,915.

Phenylamidinoureas have also been reported as possessing antisecretory, antispasmodic, antiulcerogenic, anesthetic, antidiarrheal and antihypertensive activity in a series of recent patents and publications. See: *Arzneimittel Forschung*, (Drug Research) 28 (II), 1443–1480 (1978); and U.S. Patent Nos.: 4,025,652; 4,058,557; 4,060,635; 4,088,785; 4,115,564; 4,115,647; 4,117,165; 4,147,804; 4,150,154; 4,169,115; 4,178,387; 4,204,000; and 4,220,685.

It has been found that a class of aralkyl and aralkenyl acyl guanidines capable of tautomerism possess pharmacological activity including antiprotozoal activity.

SUMMARY OF THE INVENTION

This invention relates to a method for the treatment of humans and animals afflicted with physiological disorders including protozoal infections or gastrointestinal disorders comprising administering thereto an effective therapeutic amount of a compound represented by Formula I $$R_1-\overset{R_2}{\overset{\|}{C}}-NH-\overset{NR_3}{\overset{\|}{C}}-N\overset{R_4}{\underset{R_5}{\diagdown}} \quad \text{I}$$

wherein:

$R_1$ is phenalkyl, substituted phenalkyl, phenalkenyl, substituted phenalkenyl, or a phenyl substituted 3 to 7 member heterocyclic ring which may include 1 to 4 hetero atoms of N, O or S, and containing a total of about 3 to 30 carbon atoms, and the N and S oxides thereof;

$R_2$ is oxygen or sulfur;

$R_3$ is hydrogen or alkyl;

$R_4$ and $R_5$ are hydrogen, alkyl, haloalkyl, cycloalkyl, aralkyl, alkenyl, aryl, alkynyl, alkoxy, acyl, aroyl, a heterocycle or a substituted heterocycle; or $R_4$ or $R_5$ together with the nitrogen to which they are attached form a 3 to 7 atom ring which may include 0 to 2 additional hetero atoms of N, O or S; or a nontoxic acid addition salt thereof.

Compounds according to Formula I possess useful pharmacological activity and are useful in the treatment of humans and animals suffering from physiological disorders, including gastrointestinal and cardiovascular disorders and protozoal infections including coccidiosis.

This invention also relates to a novel class of compounds useful in the aforesaid methods according to Formula I wherein $R_1$ is phenethyl, substituted phenenthyl, phenalkenyl, substituted phenalkenyl, or a phenyl substituted heterocyclic ring.

DETAILED DESCRIPTION OF THE INVENTION

The novel class of compounds of this invention is described by Formula II:

$$R_1-\overset{R_a}{\underset{R_b}{\overset{|}{\underset{|}{C}}}}-\overset{R_c}{\underset{R_d}{\overset{|}{\underset{|}{C}}}}-\overset{R_2}{\overset{\|}{C}}-NH-\overset{NR_3}{\overset{\|}{C}}-N\overset{R_4}{\underset{R_5}{\diagdown}} \quad \text{II}$$

wherein:

$R_1$ is phenyl or substituted phenyl;

$R_a$, $R_b$, $R_c$, and $R_d$ are hydrogen, lower alkyl, lower alkenyl, amino, or hydroxyl loweralkyl; or either $R_a$ and $R_c$ or $R_b$ and $R_d$ together with the carbon atoms to which they are attached form either a double bond or a 5 or 6 membered ring which may include one to four heteroatoms of N, O or S;

$R_2$ is oxygen or sulfur;

$R_3$ is hydrogen or lower alkyl;

$R_4$ and $R_5$ are hydrogen, lower alkyl, haloloweralkyl, cycloalkyl, phenalkyl, lower alkenyl, lower alkylacyl, lower alkynyl, lower alkoxy, phenyl, benzoyl, heterocycle or substituted heterocycle; or $R_4$ and $R_5$ together with the nitrogen to which they are attached form a 3 to 7 atom ring which may include 0 to 2 additional hetero atoms of N, O or S; or a nontoxic acid addition salt thereof.

An embodiment of this invention, of particular interest, is a class of compounds according to Formula II wherein:

$R_a$ and $R_c$ form a heterocycle selected from the group consisting of pyrrole, imidizole, pyrazole, pyrrolidine, pyrroline, pyridone, pyridyl, oxazolidinyl, isoxazolyl, thiazolidinyl, pyrazolidinyl, imidazolidinyl, piperidyl, piperazinyl, morpholinyl, and thiamorpholinyl;

$R_1$ is phenyl or phenyl in which one or more phenyl hydrogens is substituted by lower alkyl, lower alkenyl, lower alkynyl, halo, nitro, cyano, sulfonyl, hydroxyl, carboxyl, lower alkanoyl, lower alkoxy, aryl-loweralkoxy, haloloweralkoxy, amido, amino, loweralkylamino, loweralkoxyamino, carboloweralkoxy or aralkylamino;

$R_2$ is oxygen or sulfur;

$R_3$ is hydrogen or alkyl;

$R_4$ and $R_5$ are hydrogen, lower alkyl, haloloweralkyl, lower alkenyl, cycloalkyl, benzyl, lower alkylacyl, lower alkynyl, lower alkoxy, phenyl, benzoyl, heterocycle or substituted heterocycle; or $R_4$ and $R_5$ together with the nitrogen to which they are attached form a 3 to 7 atom ring which may include 0 to 2 additional heteroatoms of N, O or S; or a nontoxic acid addition salt thereof.

Another class of compounds of particular interest is the class of compounds according to Formula I wherein:

$R_1$ is phenethyl, substituted phenethyl, phenalkenyl, or substituted phenalkenyl.

A preferred subclass of compounds according to Formulae I and II is where:

$R_3$ and $R_4$ are hydrogen;

$R_5$ is hydrogen, lower alkyl, haloloweralkyl, lower alkenyl, lower alkynyl, lower alkanoyl, or lower alkoxy.

The nomenclature used to describe the acyl guanidines disclosed herein is as follows:

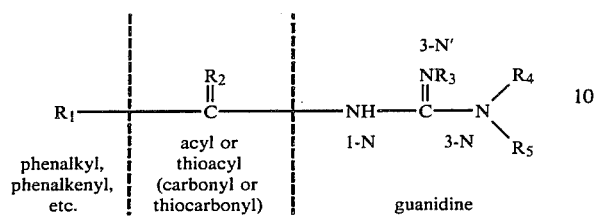

wherein: the 1-N, 3-N, and 3-N' nitrogen positions on the quanidine are designated as shown above.

For purposes of convenience, and as will be evident from its use context, the term "acyl guanidine" is used to encompass within its meaning "thioacyl guanidine".

In any discussion of the true structure of an acyl guanidine, tautomerism must be considered. The acyl guanidine side chain of the compounds of the present invention can be legitimately represented in any one of several tautomeric forms. In solution, one form may predominate over another depending upon the degree and location of substitution and on the nature of the solvent. The rates of conversion of one tautomer to another will depend upon the nature of the solvent, the degree of hydrogen bonding permitted, the temperature, and possibly other factors (such as pH, trace impurities and the like).

To illustrate what is meant by this, a number of likely structures are here shown for just one of the compounds of this invention:

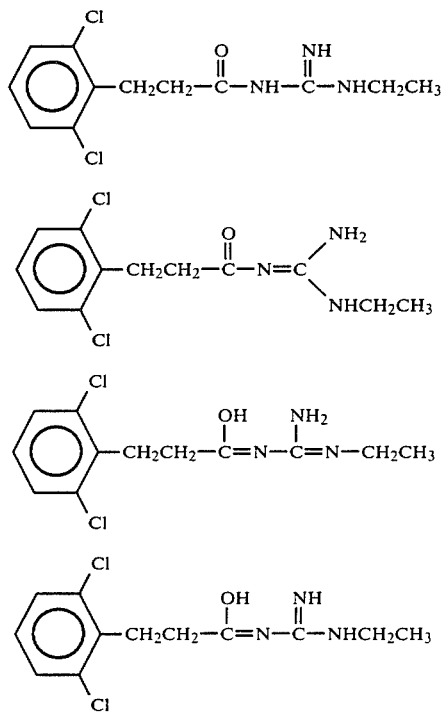

Of course, other structures are possible, such as those with hydrogen bonding.

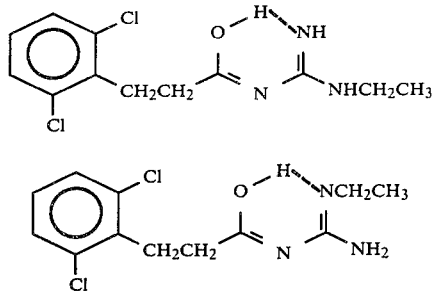

As employed above and throughout the disclosure, the following terms, unless otherwise indicated, shall be understood to have the following meanings:

"Alkyl" means a saturated aliphatic hydrocarbon which may be either straight- or branched-chained. Preferred alkyl groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" means an alkyl group as above, having 1 to about 6 carbon atoms. Examples of lower alkyl groups are methyl, ethyl, n-propyl, isopropyl, butyl, sec-butyl, tert-butyl, n-pentyl, isopentyl and neopentyl.

"Cycloalkyl" means an aliphatic monocyclic saturated carbocyclic group. Preferred groups have about 3 to about 6 carbon atoms, and exemplary groups include cyclopropyl, cyclopentyl and cyclohexyl.

"Alkenyl" means an unsaturated aliphatic hydrocarbon. Preferred groups have no more than about 12 carbon atoms. Exemplary groups include any structural and geometric isomers of ethenyl, propylenyl, butenyl, pentenyl, hexenyl, heptenyl, octenyl, nonenyl, decenyl, undecenyl, and dodecenyl or butadienyl, pentadienyl etc.

"Lower alkenyl" means alkenyl of about 2 to about 6 carbon atoms. Preferred groups include ethylene, propylene, butylene, isobutylene, and all structural and geometrical isomers thereof.

"Alkynyl" means an unsaturated aliphatic hydrocarbon. Preferred groups have no more than about 12 carbon atoms and contain one or more triple bonds, including any structural or geometric isomers of ethynyl, propynyl, butynyl, pentynyl, hexynyl, heptynyl, octynyl, nonynyl, decynyl, undecynyl, dodecynyl, etc.

"Lower alkynyl" means alkynyl of about 2 to about 6 carbon atoms. Preferred groups include structural and geometric isomers of propargyl, butynyl, and pentynyl.

"Aryl" means phenyl and substituted phenyl.

"Substituted phenyl" means a phenyl group in which one or more of the hydrogens has been replaced by the same or different substituents including halo, lower alkyl, lower alkenyl, lower alkynyl, halo-lower alkyl, nitro, amino, acylamino, hydroxy, carboxyl, lower alkoxy, aryl lower alkoxy, acyloxy, lower alkanoyl, cyano, halo-lower alkoxy, carbolower alkoxy, amido, loweralkylamino, lower alkoxyamino, aralkylamino, or lower alkyl sulfonyl.

"Aralkyl" means an alkyl group in which one or more hydrogens is substituted by an aryl group. Preferred groups are phenalkyl and substituted phenalkyl.

"Phenalkyl" means an alkyl group substituted by a phenyl group.

"Substituted phenalkyl" means a phenalkyl group in which one or more phenyl hydrogens are replaced as given above with respect to substituted phenyl.

"Phenalkenyl" is an alkenyl group substituted by phenyl.

"Substituted phenalkenyl" mean a phenalkenyl group in which the phenyl group is substituted as given above with respect to substituted phenyl.

"Heterocyclic ring" or "heterocycle" means a 3, 5, 6 or 7 membered ring having 1 to 3 hereto atoms which may be nitrogen, oxygen or sulfur, including pyrrole, pyrrolidine, pyridone, heptamethyleneiminyl, pyrazole, pyridyl, pyrimidyl, pyrazolyl, imidazolyl, isoxazolyl, furyl, thienyl, oxazolyl, thiazolyl, piperidyl, morpholinyl, oxazolidinyl, thiazolidinyl, pyrazolidinyl, imidazolidinyl, piperazinyl, thiamorpholinyl, azepinyl, and ethyleneiminyl.

"Substituted heterocycle" means a heterocycle in which one or more of the hydrogens on the ring carbons have been replaced by substituents as given above with respect to substituted phenyl.

The terms "halo" and "halogen" include all four halogens; namely, fluorine, chlorine, bromine and iodine. The halo alkyls, halophenyl and halo-substituted pyridyl groups having more than one halo substituent which may be the same or different such as trifluoromethyl, 1-chloro-2-bromo-ethyl, chlorophenyl, and 4-chloropyridyl.

"Acyl" means an organic carbonyl radical of a lower alkanoic acid. Preferred acyl groups are lower alkanoyl groups such as acetyl and propionyl.

"Aroyl" means an aromatic acid radical such as benzoyl, toluoyl.

"Lower alkanoyl" means the acyl radical of a lower alkanoic acid such as acetyl, propionyl, butyryl, valeryl, stearoyl, and the like.

"Alkoxy" means an alkyloxy group and includes hydroxy alkyl groups. Preferred lower alkoxy groups are methoxy, ethoxy, n-propoxy, and i-propoxy, isobutoxy, n-butoxy, and t-butoxy.

The preferred "aryl" group is phenyl.

The preferred "aralkyl" groups are benzyl and phenethyl.

The preferred "halo lower alkyl" group is trifluoromethyl.

The preferred "halo lower alkoxy" group is trifluoromethoxy.

The acyl guanidines may be prepared by the following general synthesis.

Reaction of an appropriately substituted acetyl chloride or thioacetyl chloride with an appropriately substituted guanidine yields the acyl guanidine according to Formulae I or II (Scheme I).

SCHEME I $$R_1-\overset{X}{\overset{\|}{C}}-Cl + NH_2-\overset{NR_3}{\overset{\|}{C}}-NR_4R_5 \longrightarrow$$

$$R_1-\overset{X}{\overset{\|}{C}}-NH-\overset{NR_3}{\overset{\|}{C}}-N\overset{R_5}{\underset{R_4}{\diagdown}}$$

X may be O or S.

The acyl chloride and thioacyl chloride starting materials are known or may be prepared according to methods known to one skilled in the art.

Alternatively, activated acyl reagents, such as carbamates or thiocarbamates may be used.

The guanidine is preferably prepared in situ by neutralizing the guanidine acid addition salt.

The condensation reaction is preferably run under dry conditions. However, minute traces of water may be tolerated in the reaction mixture. The reaction may be run at room temperature and may last anywhere from a few hours to a few days or the reaction temperature may be raised to that of the boiling point of the reaction media and refluxed for a few minutes to a few hours. Of course, the particular compound being prepared, the solvent and reagents being used will influence the temperature, time and yield of the reaction.

The reaction solvent is preferably a polar aprotic solvent, such as acetone or tetrahydrofuran.

The following are detailed examples which show the preparation of compounds useful in the method of this invention.

EXAMPLE 1

The Preparation of 1-Methyl-3-Phenyl-Acetylguanidine

A 50% aqueous solution of sodium hydroxide (8.80 g), methylguanidine sulfate (13.44 ), and 100 ml of acetone, are stirred for 2-½ hrs at RT. The resulting mixture is then treated with anhydrous sodium sulfate (6.0 g) and stirring is continued for 1 hr. A solution of phenylacetyl chloride (7.73 g) in 50 ml acetone is added dropwise over a period of ½ hr. The reaction mixture is stirred overnight at RT. The reaction mixture is diluted with 100 ml of saturated aqueous sodium bicarbonate and the acetone is evaporated. The mixture is diluted with 100 ml H$_2$O and extracted with two 100 ml portions of methylene chloride. The organic extract is dried with sodium sulfate, filtered and the filtrate evaporated in vacuo. The residual solid is dissolved in methanol and the solution acidified with methanolic hydrochloric acid. The acidic solution is evaporated in vacuo and the residue triturated in diethyl ether affording a tan solid which is recrystallized from acetone as a white solid, M.P. 131° C.

EXAMPLE 2

The Preparation of 1-(4-Methoxyphenyl-Acetyl)-3-Methylguanidine Hydrochloride

Step I. 4-methoxyphenylacetychloride

Oxalyl chloride (95.2 g) is added to a stirred solution of 4-methoxyphenylacetic acid (83.09 g) in 500 ml of methylene chloride. The resulting mixture is stirred for ½ hr at RT and evaporated overnight. After cooling to room temperature, the solvent is evaporated in vacuo to afford 92.85 g (100%) of crude product as an orange-red liquid.

Step II. 1-(4-methoxyphenylacetyl)-3-methylguanidine hydrochloride

A mixture of 8.80 g of a 50% aqueous sodium hydroxide solution, 13.44 g of methylguanidine sulfate and 100 ml acetone is stirred for 2½ hrs at RT. 6.0 g of anhydrous sodium sulfate are added to the mixture, and stirring continued for 1 hr. 4-methoxyphenylacetyl chloride (9.23 g) in 50 ml acetone is added, and the reaction mixture stirred overnight at RT. The reaction mixture is filtered and the filtrate is diluted with 100 ml of saturated aqueous sodium bicarbonate and the acetone evaporated in vacuo. The aqueous phase is diluted with 100 ml H$_2$O and extracted with two 100 ml portions of methylene chloride. The combined organic extracts are dried with sodium sulfate, filtered and concentrated in vacuo. The resulting preccipitate is dissolved in a small volume of methanol and acidified with ethereal hydrochloric acid. The solvent is evaporated in vacuo, and the residue stirred with 200 ml of diethyl ether. The solid is collected, dried in air and recrystallized from acetonitrile to afford 4.80 g of white solid, M.P. 189° C.

EXAMPLE 3

The Preparation of
1-(4-Methoxyphenylacetyl)-3-Isopropylguanidine Hydrochloride

A mixture containing methylguanidine sulfate (16.52 g), 8.8 g of aqueous sodium hydroxide (50% solution), and 100 ml of acetone, is stirred for 2½ hrs at RT. Anhydrous sodium sulfate (6.0 g) is added, and stirring continued for 1 hr. A solution of 4-methoxyphenylacetylchloride (9.23 g) in 50 ml of acetone is added dropwise and the reaction mixture stirred overnight at RT. The reaction mixture is filtered and the filtrate diluted with 100 ml of saturated aqueous sodium bicarbonate. The acetone is evaporated in vacuo, and the aqueous residue diluted with 100 ml H$_2$O and extracted with two 100 ml portions of methylene chloride. The combined organic extracts are dried with sodium sulfate, filtered and concentrated in vacuo. The concentrate is acidified with ethereal hydrochloric acid and the solvent evaporated in vacuo. The residue is stirred in 200 ml of diethyl ether. The resultant solid is collected, washed with diethyl ether, dried in air and recrystallized, affording 5.43 g of a white solid, M.P. 125°–128° C.

EXAMPLE 4

The Preparation of
1-(4-Chlorophenylacetyl)-3-Ethylguanidine Hydrochloride

Step I. 4-chlorophenylacetyl chloride

To a stirred suspension of 4-chlorophenylacetic acid (85.3 g) in 500 ml of toluene, 45 ml of thionyl chloride (74.4 g) are added. The resulting mixture is stirred at RT, heated slowly to boiling, and stirred overnight under reflux. After cooling the reaction mixture to RT, the solvent is evaporated in vacuo. Distillation of the residue affords 38.15 g of a red liquid.

Step II. 1-(4-chlorophenylacetyl)-3-ethylguanidine

A mixture of a 50% aqueous solution of sodium hydroxide (8.80 g), ethylguanidine sulfate (14.98 g), and 100 ml of acetone is stirred for 2½ hrs at RT. The reaction mixture is treated with anhydrous sodium sulfate (6.0 g) and stirred for 1 hr. A solution of 4-chlorophenylacetylchloride (9.45 g) in 50 ml acetone is added to the reaction mixture dropwise and the mixture stirred overnight. The mixture is filtered, and the filtrate diluted with 100 ml of saturated aqueous sodium bicarbonate and the acetone evaporated in vacuo. The aqueous mixture is diluted with 100 ml of H$_2$O and extracted with two 100 ml portions of methylene chloride. The combined extracts are dried with sodium sulfate, filtered and evaporated in vacuo. The resulting solution is treated with ethereal hydrochloric acid, and the solvent evaporated in vacuo. The residue is stirred with 200 ml of diethyl ether for ½ hr. The diethyl-ether insoluble solid is collected and dried in air. The product is recrystallized from CH$_3$CN to afford 6.03 g of white crystalline solid, M.P. 146°–147° C.

EXAMPLE 5

The Preparation of
1-(4-Chlorophenylacetyl)-3-Methylguanidine Hydrochloride 8.80 g of a 50% aqueous sodium hydroxide solution, methylguanidine sulfate (13.44 g), and 100 ml of acetone, are stirred for 2½ hrs at RT. The resulting mixture is then treated with anhydrous sodium sulfate (6.0 g), and stirring is continued for 1 hr. A solution of 4-chlorophenylacetylchloride (9.45 g) in 50 ml of acetone is added to the mixture dropwise, and stirring continued overnight at RT. The reaction mixture is filtered, the filtrate diluted with 100 ml of saturated sodium bicarbonate and the acetone evaporated in vacuo. The aqueous residue is diluted with 100 ml of H$_2$O and extracted with three 100 ml portions of methylene chloride. The combined organic extract is dried with sodium sulfate, filtered and concentrated in vacuo. The resulting yellow solution is treated with ethereal hydrochloric acid and evaporated in vacuo. The residue is stirred with diethyl ether for ½ hr. The diethyl ether insoluble solid is collected and dried in air. The product is recrystallized from acetonitrile to afford 5.66 g of a white crystalline solid, M.P. 183°–184° C.

EXAMPLE 6

The Preparation of
1-(4-chlorophenylacetyl)-3-Isopropylguanidine Hydrochloride 8.80 g of a 50% aqueous sodium hydroxide solution, isopropylguanidine (16.52 g), and 100 ml of acetone, are stirred for 2½ hrs at RT. The resulting mixture is then treated with anhydrous sodium sulfate (6.0 g), and stirring is continued for 1 hr. A solution of 4-chlorophenylacetyl (9.45 g) in 50 ml of acetone is added dropwise to the mixture over a period of 1 hr, and stirring continued overnight at RT. The reaction mixture is filtered and the filtrate diluted with 100 ml of saturated aqueous sodium bicarbonate. The acetone is evaporated in vacuo, and the aqueous residue diluted with 100 ml of H$_2$O and extracted with two 100 ml portions of methylene chloride. The combined extracts are dried with sodium sulfate, filtered and concentrated in vacuo. The resulting solution is acidified with ethereal hydrochloric acid and the solvent evaporated in vacuo. The residual oil is stirred with 200 ml of diethyl ether for 2 hrs. The resulting solid is washed with diethyl ether, dried in air and recrystallized from acetone to afford 6.5 g of a white solid, M.P. 162°–163.5° C.

EXAMPLE 7

The Preparation of
1-(3-Methoxyphenylacetyl)-3-Ethylguanidine Hydrochloride

Step I. 3-methoxyphenylacetyl chloride

Oxalyl chloride (57.1 g) is added to a stirred solution of 3-methoxyphenylacetic acid (49.85 g) in 300 ml of methylene chloride. The reaction mixture is stirred for 1½ hr at RT, refluxed overnight, and then evaporated in vacuo. The residual product is used in the next step.

Step II. 1-(3-methoxyphenylacetyl)-3-ethylguanidine 8.80 g of a 50% aqueous sodium hydroxide solution, ethylguanidine sulfate (14.98 g), and 100 ml of acetone are stirred for 2½ hrs at RT. The resulting mixture is treated with anhydrous sodium sulfate (6.0 g) and stirring continued for 1 hr. A solution of 3-methoxyphenylacetyl chloride (9.23 g) in 50 ml acetone is added to the mixture dropwise and the reaction mixture stirred overnight at RT. The mixture is filtered and the filtrate diluted with saturated aqueous sodium bicarbonate. The acetone residue is evaporated in vacuo. The aqueous residue is diluted with 100 ml of H$_2$O and extracted with two 100 ml portions of methylene chloride. The combined extracts are dried with sodium sulfate, filtered and concentrated in vacuo. The resulting solution is acidified with ethereal hydrochloric acid and the solvent evaporated in vacuo. The residue is stirred with 200 ml of diethyl ether and the solid collected, washed with diethyl ether and recrystallized from acetone, affording the product, M.P. 108°–110° C.

EXAMPLE 8

The Preparation of
1-(3-Methoxyphenylacetyl)-3-Isopropylguanidine Hydrochloride 8.80 g of a 50% aqueous sodium hydroxide solution, isopropylguanidine sulfate (16.52 g), and 100 ml of acetone are stirred for 2½ hrs at RT. The resulting mixture is then treated with anhydrous sodium sulfate (6.0 g) and stirring continued for 1 hr. A solution of 3-methoxyphenylacetyl chloride in 50 ml acetone is added to the mixture dropwise and the reaction mixture stirred at RT over the weekend. The mixture is filtered and the filtrate diluted with 100 ml of saturated aqueous sodium bicarbonate. The acetone solvent is evaporated in vacuo, the aqueous residue diluted with 100 ml of H$_2$O and extracted with two 100 ml portions of methylene chloride. The combined organic extract is dried with sodium sulfate, filtered and evaporated in vacuo. The residual oil is stirred with 200 ml of diethyl ether. The resulting solid is collected, washed and diethyl ether, dried in air and recrystallized to afford 6.66 g of product, M.P. 156°–158° C.

EXAMPLE 9

The Preparation of
1-(2-Methoxyphenylacetyl)-3-Ethylguanidine Hydrochloride

Step I. 2-methoxyphenylacetyl chloride 39.5 ml of an oxalyl chloride solution (57.1 g) are added to a stirred solution of 2-methoxyphenylacetic acid (49.85 g) in 300 ml of methylene chloride. The reaction mixture is stirred under reflux overnight, cooled and the solvent evaporated in vacuo to afford 56.09 g of crude acid chloride.

Step II. 1-(2-methoxyphenylacetyl)-3-ethylguanidine 8.80 g of a 50% aqueous sodium hydroxide solution, ethylguanidine sulfate (14.98 g) and 100 ml of acetone, are stirred for 2½ hrs at RT. The resulting mixture is treated with anhydrous sodium sulfate (6.0 g) and stirring continued for 1 hr. A solution of 2-methoxyphenylacetyl chloride (9.23 g) in 50 ml of acetone is added to the mixture dropwise and stirring is continued overnight at RT. The reaction mixture is filtered, the filtrate diluted with 100 ml of saturated aqueous sodium bicarbonate and the acetone evaporated in vacuo. The residue is diluted with 100 ml H$_2$O and extracted with two 100 ml portions of methylene chloride. The extract is dried with sodium sulfate, filtered and concentrated in vacuo. The concentrate is acidified with ethereal hydrochloric acid and the solvent evaporated in vacuo. After stirring the residue with 200 ml of diethyl ether, the solid is collected, washed with diethyl ether and dried in air. The residual solid is recrystallized from acetone affording a white solid, M.P. 127°–128° C.

EXAMPLE 10

The Preparation of
1-(2-Methoxyphenylacetyl)-3-Isopropyl Guanidine Hydrochloride 8.80 g of a 50% aqueous sodium hydroxide solution, isopropylguanidine sulfate (16.52 g) and 100 ml of acetone, are stirred for 2½ hrs at RT. The resulting mixture is treated with anhydrous sodium sulfate (6.0 g) and stirring continued for 1 hr. A solution of 2-methoxyphenylacetyl chloride (9.23 g) in 50 ml of acetone is added to the mixture dropwise and the mixture stirred overnight at RT. The resulting mixture is filtered and the filtrate diluted with 100 ml of saturated aqueous sodium bicarbonate. The acetone solvent is evaporated in vacuo. The residue is diluted with 100 ml H$_2$O and extracted with two 100 ml portions of methylene chloride. The extract is dried with sodium sulfate, filtered and concentrated in vacuo. The concentrate is acidified with ethereal hydrochloric acid and the solvent evaporated in vacuo. The residue is stirred with 200 ml of diethyl ether, the solid collected and dried in air. The residual solid is recrystallized from acetone to afford 6.4 g of a white crystalline product, M.P. 154°–156° C.

EXAMPLE 11

The Preparation of
1-Ethyl-3-(2,6-Dichlorophenylacetyl)Guanidine Hydrochloride

Step I. The preparation of 2,6-dichlorophenylacetyl chloride 30.93 g of thionyl chloride are added dropwise to a warmed, mechanically stirred mixture of 45.12 g of 2,6-dichlorophenylacetic acid in 125 ml of toluene. The reaction mixture is then maintained at reflux for 5 hrs and cooled overnight at RT. The reaction mixture is concentrated in vacuo and the concentrate dissolved in hot petroleum ether and the solids filtered. The filtrate is concentrated in vacuo to give a dark amber liquid, which is distilled to give a clear pinkish liquid.

Step II. 1-ethyl-3-(2,6-dichlorophenylacetyl)guanidine hydrochloride

A mixture of 30.4 g of a 50% aqueous sodium hydroxide solution, 51.74 g of ethylguanidine sulfate and 800 ml of tetrahydrofuran is stirred for 45 minutes at RT. 60 g of anhydrous sodium sulfate are added and stirring continued for 45 minutes. A solution of 2,6-dichlorophenylacetyl chloride (41.69 g) in 200 ml of tetrahydrofuran is added dropwise and the reaction mixture stirred another day, filtered and concentrated in vacuo. The resulting yellow oil is partitioned between 250 ml of methylene chloride and 250 ml of H$_2$O. After separating the two layers, the aqueous portion is extracted with methylene chloride, the combined organic extract dried over magnesium sulfate, filtered and acidified with hydrochloric acid/methanol. The acidified solution is concentrated in vacuo to afford a white solid which is recrystallized from acetonitrile/methanol affording a white solid, M.P. 228°–230° C.

EXAMPLE 12

The Preparation of 1-Propyl-3-(2,6-Dichlorophenylacetyl)Guanidine Hydrochloride A mixture of 12.02 g of propylguanidine sulfate, 6.4 g of a 50% aqueous sodium hydroxide solution and 30 ml tetrahydrofuran is stirred for 2 hrs at RT. 5 g of sodium sulfate are added followed by the dropwise addition of a solution of 2,6-dichlorphenyl acetyl chloride (8.94 g) in 16 ml of tetrahydrofuran and stirred overnight. The mixture is evaporated to dryness, the residue suspended in 50 ml of water and stirred for 1 hr at RT. The mixture is extracted with chloroform, the extract is dried with magnesium sulfate, filtered and evaporated. The oily residue is dried in vacuo to afford 5.44 g of a pale yellow resin. The resin is taken up in chloroform and brought to pH 2 with ethereal hydrochloric acid. The resulting solution is evaporated to dryness and the residue recrystallized from acetonitrile/methanol. The crystals are collected by filtration, washed with acetonitrile and dried in vacuo to afford 3.87 g of white crystals, M.P. 217°–219° C.

EXAMPLE 13

The Preparation of 1,1-Dimethyl-3-(2,6-Dichlorophenylacetyl)Guanidine Hydrochloride 10.89 g of 1,1-dimethylguanidine sulfate, 6.4 g of a 50% sodium hydroxide solution and 30 ml tetrahydrofuran are stirred for 2 hrs at RT. 5 g of anhydrous sodium sulfate are added, followed by the dropwise addition of a solution of 2,6-dichlorodichorophenylacetyl chloride (8.94 g) in 16 ml of tetrahydrofuran. The resulting mixture is stirred overnight at RT. The reaction mixture is evaporated to dryness and the residue stirred with 50 ml H$_2$O at RT for 1 hr. The mixture is filtered and the solid washed with H$_2$O and dried in vacuo. The resulting solid is extracted with 50 ml of boiling acetonitrile, filtered while hot, and the filtrate evaporated in vacuo. The resulting white solid is extracted with hot chloroform, filtered and the filtrate evaporated to dryness. The residue is recrystallized from benzene/chloroform. The solvent is removed and the residue dried in vacuo. The resulting material is taken up in ca 100 ml of chloroform, washed with 100 ml H$_2$O and the chloroform layer separated, dried with magnesium sulfate and evaporated to dryness to afford a yellow oil. The yellow oil is taken up in chloroform and the resulting solution brought to pH 2 with methanolic hydrochloric acid. The solution is evaporated to dryness and the residual yellow solid crystallized to afford 4.38 g of tan crystalline solid, M.P. 225.5°–227° C.

The following are examples of the preparation of compounds within the compound aspect of the present invention.

EXAMPLE 14

The Preparation of 1-Cinnamoyl-3-Isobutylguanidine Hydrochloride

A mixture of 7.95 g of a 50% aqueous sodium hydroxide solution, isobutylguanidine sulfate (16.32 g), and 120 ml of tetrahydrofuran is stirred for 45 minutes. 12 g anhydrous sodium sulfate are added to the mixture and stirring continued 45 minutes. A solution of cinnamoyl chloride (8.28 g) in anhydrous tetrahydrofuran is slowly added dropwise to the reaction mixture and stirring continued for 48 hrs. The reaction mixture is filtered and concentrated in vacuo. The resultant yellow solid is partitioned between 150 ml of water and 125 ml of methylene chloride. The aqueous layer is extracted with methylene chloride and the combined organic extract dried, filtered, acidified with hydrochloric acid/methanol and concentrated in vacuo. The residue is twice recrystallized from hot acetonitrile/methanol to afford a white solid, M.P. 193°–194.5° C.

EXAMPLE 15

The Preparation of 1-(2,6-Dichlorocinnamoyl)-3-Ethylguanidine Hydrochloride

Step I. The preparation of 2,6-dichlorocinnamoyl chloride

A solution of 20% thionyl chloride in toluene is added dropwise to a magnetically stirred, warmed mixture of 2,6-dichlorocinnamic acid (20.74 g) in toluene (119 ml) and the mixture brought to reflux for 6 hrs after it clears to a yellow haze. The reaction mixture is cooled overnight, filtered and concentrated in vacuo to afford a pale yellow solid, M.P. 64.5°–66° C.

Step II. 1-(2,6-dichlorocinnamoyl)-3-ethylguanidine hydrochloride

A mixture of 7.48 g of a 50% sodium hydroxide solution, 12.72 g of ethylguanidine sulfate, and 120 ml of tetrahydrofuran is stirred for 45 minutes. Anhydrous sodium sulfate (12 g) is added to the mixture and stirred for 40 minutes. 11.0 g of 2,6-dichlorocinnamoyl chloride in 40 ml of anhydrous tetrahydrofuran are added dropwise to the resulting mixture and stirred overnight. The reaction mixture is filtered, concentrated in vacuo and the resulting yellow oil partitioned between 100 ml of methylene chloride and 150 ml of H$_2$O. The aqueous layer is extracted with methylene chloride, the combined organic extract is dried over anhydrous magnesium sulfate, filtered and concentrated in vacuo to a yellow oil. The resulting oil crystallizes on standing. The crystallized solid is dissolved in hot acetonitrile, filtered and recrystallized. The white solid is collected and dried in air, M.P. 166°–171° C.

EXAMPLE 16

The Preparation of 1-(2,6-Dichlorocinnamoyl)-3-Isobutylguanidine Hydrochloride A mixture of 7.62 g of a 50% aqueous sodium hydroxide solution, 15.65 g isobutylguanidine sulfate and 120 ml of tetrahydrofuran is stirred for 45 minutes. 12 g of anhydrous sodium sulfate are added to the mixture and stirring continued for 40 minutes. A solution of 2,6-dichlorocinnamoyl chloride (11.22 g) in 40 ml of anhydrous tetrahydrofuran is added dropwise, and the reaction mixture stirred overnight. The yellow reaction mixture is filtered, concentrated in vacuo and the resulting yellow oil partitioned between 100 ml of methylene chloride and 150 ml of H₂O. The aqueous layer is extracted with methylene chloride, the combined organic extract dried over anhydrous magnesium sulfate, filtered and concentrated in vacuo to a yellow oil. The resulting oil is dissolved in hot acetonitrile/methanol, filtered and evaporated on a hot plate. A white solid is collected, M.P. 178°–180° C.

EXAMPLE 17

The Preparation of 1-(5-Methyl-3-Phenyl-4-Isoxazoloyl)-3-Ethylguanidine Hydrochloride Step I. 5-methyl-3-phenyl-4-isoxazoloyl chloride A mixture of 111.76 g of 5-methyl-3-phenyl-4-isoxazoloyl carboxylic acid, 6 drops of pyridine and 29.5 ml of thionyl chloride is stirred under reflux for 4 hrs. The excess thionyl chloride is evaporated in vacuo. Distillation of the residue yields 113.74 g of yellow liquid.

Step II. 1-(5-methyl-3-phenyl-4-isoxazoloyl)3-ethylguanidine

A mixture of 8.80 g of an aqueous sodium hydroxide solution (50%), ethylguanidine sulfate (14.98 g), and 100 ml of acetone, are stirred for 2½ hrs at RT. The resulting mixture is then treated with anhydrous sodium sulfate (6.0 g) and stirring is continued for 1 hr. A solution of 5-methyl-3-phenyl-4-isoxazoloyl chloride (11.08 g) in 50 ml acetone is added dropwise and the resulting mixture is stirred overnight at RT. The reaction mixture is filtered, the filtrate diluted with 100 ml of saturated aqueous sodium bicarbonate and the acetone evaporated in vacuo. The aqueous residue is diluted with 100 ml H₂O and extracted with two 100 ml portions of methylene chloride. The combined organic extract is dried, filtered and concentrated in vacuo. The residue is acidified with ethereal hydrochloric acid and evaporated in vacuo. The residue is stirred with 200 ml of diethyl ether, the solid collected and washed with diethyl ether. Recrystallization from acetonitrile affords 11.7 g of white crystalline product, M.P. 215° C.

Representative examples of the compounds of this invention and compounds useful in the method of this invention are listed in Tables I and I-A.

TABLE I 1-(2-chlorophenylacetyl)-3-methyl guanidine
1-(2-methylphenylacetyl)-3-methyl guanidine
1-(2-chloro-6-methylphenylacetyl)-3-methyl guanidine
1-(2-trifluoromethylphenylacetyl)-3-methyl guanidine
1-(2,6-dimethylphenylacetyl)-3-methyl guanidine
1-[2-(2-chlorophenyl)propionyl]-3-methyl guanidine
1-[2-(2-methylphenyl)propionyl]-3-methyl guanidine
1-[2-(2-chloro-6-methylphenyl)propionyl]-3-methyl guanidine
1-[2-(2-trifluoromethylphenyl)propionyl]-3-methyl guanidine
1-[2-(2,6-dimethylphenyl)propionyl]-3-methyl guanidine
1-[2-chlorocinnamoyl]-3-methyl guanidine
1-[2-methylcinnamoyl]-3-methyl guanidine
1-[2-chloro-6-methylcinnamoyl]-3-methyl guanidine
1-[2-trifluoromethylcinnamoyl]-3-methyl guanidine
1-[2,6-dimethylcinnamoyl]-3-methyl guanidine
1-[5-methyl-3-(2-chlorophenyl)-4-isoxazoloyl]-3-methyl guanidine
1-[5-methyl-3-(2-methylphenyl)-4-isoxazoloyl]-3-methyl guanidine
1-[5-methyl-3-(2-chloro-6-methylphenyl)-4-isoxazoloyl]-3-methyl guanidine
1-[5-methyl-3-(2-trifluoromethylphenyl)-4-isoxazoloyl]-3-methyl guanidine
1-[5-methyl-3-(2,6-dimethylphenyl)-4-isoxazoloyl]-3-methyl guanidine
1-(2-chlorophenylacetyl)-3-allyl guanidine
1-(2-methylphenylacetyl)-3-allyl guanidine
1-(2-chloro-6-methylphenylacetyl)-3-allyl guanidine
1-(2-trifluoromethylphenylacetyl)-3-allyl guanidine
1-(2,6-dimethylphenylacetyl)-3-allyl guanidine
1-[2-(2-chlorophenyl)propionyl]-3-allyl guanidine
1-[2-(2-methylphenyl)propionyl]-3-allyl guanidine
1-[2-(2-chloro-6-methylphenyl)propionyl]-3-allyl guanidine
1-[2-(2-trifluoromethylphenyl)propionyl]-3-allyl guanidine
1-[2-(2,6-dimethylphenyl)propionyl]-3-allyl guanidine
1-[2-chlorocinnamoyl]-3-allyl guanidine
1-[2-methylcinnamoyl]-3-allyl guanidine
1-[2-chloro-6-methylcinnamoyl]-3-allyl guanidine
1-[2-trifluoromethylcinnamoyl]-3-allyl guanidine
1-[2,6-dimethylcinnamoyl]-3-allyl guanidine
1-[5-methyl-3-(2-chlorophenyl)-4-isoxazoloyl]-3-allyl guanidine
1-[5-methyl-3-(2-methylphenyl)-4-isoxazoloyl]-3-allyl guanidine
1-[5-methyl-3-(2-chloro-6-methylphenyl)-4-isoxazoloyl]-3-allyl guanidine
1-[5-methyl-3-(2-trifluoromethylphenyl)-4-isoxazoloyl]-3-allyl guanidine
1-[5-methyl-3-(2,6-dimethylphenyl)-4-isoxazoloyl]-3-allyl guanidine
1-(2-chlorophenylacetyl)-3-ethyl guanidine
1-(2-methylphenylacetyl)-3-ethyl guanidine
1-(2-chloro-6-methylphenylacetyl)-3-ethyl guanidine
1-(2-trifluoromethylphenylacetyl)-3-ethyl guanidine
1-(2,6-dimethylphenylacetyl)-3-ethyl guanidine
1-[2-(2-chlorophenyl)propionyl]-3-ethyl guanidine
1-[2-(2-methylphenyl)propionyl]-3-ethyl guanidine
1-[2-(2-chloro-6-methylphenyl)propionyl]-3-ethyl guanidine
1-[2-(2-trifluoromethylphenyl)propionyl]-3-ethyl guanidine
1-[2-(2,6-dimethylphenyl)propionyl]-3-ethyl guanidine
1-[2-chlorocinnamoyl]-3-ethyl guanidine
1-[2-methylcinnamoyl]-3-ethyl guanidine
1-[2-chloro-6-methylcinnamoyl]-3-ethyl guanidine
1-[2-trifluoromethylcinnamoyl]-3-ethyl guanidine
1-[2,6-dimethylcinnamoyl]-3-ethyl guanidine
1-[5-methyl-3-(2-chlorophenyl)-4-isoxazoloyl]-3-ethyl guanidine
1-[5-methyl-3-(2-methylphenyl)-4-isoxazoloyl]-3-ethyl guanidine
1-[5-methyl-3-(2-chloro-6-methylphenyl)-4-isoxazoloyl]-3-ethyl guanidine
1-[5-methyl-3-(2-trifluoromethylphenyl)-4-isoxazoloyl]-3-ethyl guanidine
1-[5-methyl-3-(2,6-dimethylphenyl)-4-isoxazoloyl]-3-ethyl guanidine
1-(2-chlorophenylacetyl)-3-N,N'-dimethyl guanidine
1-(2-methylphenylacetyl)-3-N,N'-dimethyl guanidine
1-(2-chloro-6-methylphenylacetyl)-3-N,N'-dimethyl guanidine 1-(2-trifluoromethylphenylacetyl)-3-N,N'-dimethyl guanidine
1-(2,6-dimethylphenylacetyl)-3-N,N'-dimethyl guanidine
1-[2-(2-chlorophenyl)propionyl]-3-N,N'-dimethyl guanidine
1-[2-(2-methylphenyl)propionyl]-3-N,N'-dimethyl guanidine
1-[2-(2-chloro-6-methylphenyl)propionyl]-3-N,N'-dimethyl guanidine
1-[2-(2-trifluoromethylphenyl)propionyl]-3-N,N'-dimethyl guanidine
1-[2-(2,6-dimethylphenyl)propionyl]-3-N,N'-dimethyl guanidine
1-[2-chlorocinnamoyl]-3-N,N'-dimethyl guanidine
1-[2-methylcinnamoyl]-3-N,N'-dimethyl guanidine
1-[2-chloro-6-methylcinnamoyl]-3-N,N'-dimethyl guanidine
1-[2-trifluoromethylcinnamoyl]-3-N,N'-dimethyl guanidine
1-[2,6-dimethylcinnamoyl]-3-N,N'-dimethyl guanidine
1-[5-methyl-3-(2-chlorophenyl)-4-isoxazoloyl]-3-N,N'-dimethyl guanidine
1-[5-methyl-3-(2-methylphenyl)-4-isoxazoloyl]-3-N,N'-dimethyl guanidine
1-[5-methyl-3-(2-chloro-6-methylphenyl)-4-isoxazoloyl]-3-N,N'-dimethyl guanidine
1-[5-methyl-3-(2-trifluoromethylphenyl)-4-isoxazoloyl]-3-N,N'-dimethyl guanidine
1-[5-methyl-3-(2,6-dimethylphenyl)-4-isoxazoloyl]-3-N,N'-dimethyl guanidine
1-(2-chlorophenylacetyl)-3-isopropyl guanidine
1-(2-methylphenylacetyl)-3-isopropyl guanidine
1-(2-chloro-6-methylphenylacetyl)-3-isopropyl guanidine
1-(2-trifluoromethylphenylacetyl)-3-isopropyl guanidine
1-(2,6-dimethylphenylacetyl)-3-isopropyl guanidine
1-[2-(2-chlorophenyl)propionyl]-3-isopropyl guanidine
1-[2-(2-methylphenyl)propionyl]-3-isopropyl guanidine
1-[2-(2-chloro-6-methylphenyl)propionyl]-3-isopropyl guanidine
1-[2-(2-trifluoromethylphenyl)propionyl]-3-isopropyl guanidine
1-[2-(2,6-dimethylphenyl)propionyl]-3-isopropyl guanidine
1-[2-chlorocinnamoyl]-3-isopropyl guanidine
1-[2-methylcinnamoyl]-3-isopropyl guanidine
1-[2-chloro-6-methylcinnamoyl]-3-isopropyl guanidine
1-[2-trifluoromethylcinnamoyl]-3-isopropyl guanidine
1-[2-2,6-dimethylcinnamoyl]-3-isopropyl guanidine
1-[5-methyl-3-(2-chlorophenyl)-4-isoxazoloyl]-3-isopropyl guanidine
1-[5-methyl-3-(2-methylphenyl)-4-isoxazoloyl]-3-isopropyl guanidine
1-[5-methyl-3-(2-chloro-6-methylphenyl)-4-isoxazoloyl]-3-isopropyl guanidine
1-[5-methyl-3-(2-trifluoromethylphenyl)-4-isoxazoloyl]-3-isopropyl guanidine
1-[5-methyl-3-(2,6-dimethylphenyl)-4-isoxazoloyl]-3-isopropyl guanidine
1-(2-chlorophenylacetyl)-3-isobutyl guanidine
1-(2-methylphenylacetyl)-3-isobutyl guanidine
1-(2-chloro-6-methylphenylacetyl)-3-isobutyl guanidine
1-(2-trifluoromethylphenylacetyl)-3-isobutyl guanidine
1-(2,6-dimethylphenylacetyl)-3-isobutyl guanidine
1-[2-(2-chlorophenyl)propionyl]-3-isobutyl guanidine
1-[2-(2-methylphenyl)propionyl]-3-isobutyl guanidine
1-[2-(2-chloro-6-methylphenyl)propionyl]-3-isobutyl guanidine
1-[2-(2-trifluoromethylphenyl)propionyl]-3-isobutyl guanidine
1-[2-(2,6-dimethylphenyl)propionyl-3-isobutyl guanidine
1-[2-chlorocinnamoyl]-3-isobutyl guanidine
1-[2-methylcinnamoyl]-3-isobutyl guanidine
1-[2-chloro-6-methylcinnamoyl]-3-isobutyl guanidine
1-[2-trifluoromethylcinnamoyl]-3-isobutyl guanidine
1-[2,6-dimethylcinnamoyl]-3-isobutyl guanidine
1-[5-methyl-3-(2-chlorophenyl)-4-isoxazoloyl]-3-isobutyl guanidine
1-[5-methyl-3-(2-methylphenyl)-4-isoxazoloyl]-3-isobutyl guanidine
1-[5-methyl-3-(2-chloro-6-methylphenyl)-4-isoxazoloyl]-3-isobutyl guanidine
1-[5-methyl-3-(2-trifluoromethylphenyl)-4-isoxazoloyl]-3-isobutyl guanidine
1-[5-methyl-3-(2,6-dimethylphenyl)-4-isoxazoloyl]-3-isobutyl guanidine
1-(2-chlorophenylacetyl)-3-propyl guanidine
1-(2-methylphenylacetyl)-3-propyl guanidine
1-(2-chloro-6-methylphenylacetyl)-3-propyl guanidine
1-(2-trifluoromethylphenylacetyl)-3-propyl guanidine
1-(2,6-dimethylphenylacetyl)-3-propyl guanidine
1-[2-(2-chlorophenyl)propionyl]-3-propyl guanidine
1-[2-(2-methylphenyl)propionyl]-3-propyl guanidine
1-[2-(2-chloro-6-methylphenyl)propionyl]-3-propyl guanidine
1-[2-trifluoromethylphenyl)propionyl-3-propyl guanidine
1-[2-(2,6-dimethylphenyl)propionyl]-3-propyl guanidine
1-[2-chlorocinnamoyl]-3-propyl guanidine
1-[2-methylcinnamoyl]-3-propyl guanidine
1-[2-chloro-6-methylcinnamoyl]-3-propyl guanidine
1-[2-trifluoromethylcinnamoyl]-3-propyl guanidine
1-[2,6-dimethylcinnamoyl]-3-propyl guanidine
1-[5-methyl-3-(2-chlorophenyl)-4-isoxazoloyl]-3-propyl guanidine
1-[5-methyl-3-(2-methylphenyl)-4-isoxazoloyl]-3-propyl guanidine
1-[5-methyl-3-(2-chloro-6-methylphenyl)-4-isoxazoloyl]-3-propyl guanidine
1-[5-methyl-3-(2-trifluoromethylphenyl)-4-isoxazoloyl]-3-propyl guanidine
1-[5-methyl-3-(2,6-dimethylphenyl)-4-isoxazoloyl]-3-propyl guanidine

TABLE I-A $$R_1-\overset{R_2}{\underset{\|}{C}}-NH-\overset{NR_3}{\underset{\|}{C}}-NR_4R_5$$

$R_2$ may be oxygen or sulfur

| $R_1$ | $R_3$ | $R_4$ | $R_5$ |
|---|---|---|---|
|  | H | H | $CH_2CH_3$ |
| 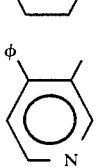 | H | H | $CH_3$ |

TABLE I-A-continued $$R_1-\overset{\overset{R_2}{\|}}{C}-NH-\overset{\overset{NR_3}{\|}}{C}-NR_4R_5$$
R₂ may be oxygen or sulfur

| R₁ | R₃ | R₄ | R₅ |
|---|---|---|---|
| 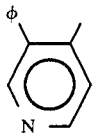 φ-pyridyl (N at position shown) | H | H | CH₂CH₃ |
| 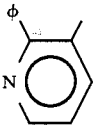 φ-pyridyl | H | H | CH₃ |
| 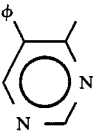 φ-pyridyl | H | H | CH₂CH₃ |
|  φ-pyridazinyl | H | H | CH₃ |
| 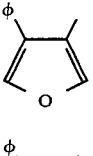 φ-furyl | H | H | CH₂CH₃ |
| 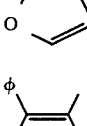 φ-furyl | H | H | CH₃ |
| 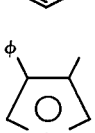 φ-furyl | H | H | CH₂CH₃ |
| 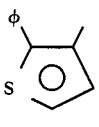 φ-thienyl | H | H | CH₃ |
| 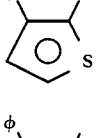 φ-thienyl | H | H | CH₂CH₃ |
| 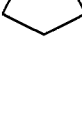 φ-thienyl | H | H | CH₃ |
|  φ-cyclopentenyl | H | H | CH₂CH₃ |
| 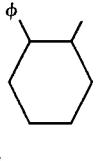 φ-cyclopentyl | H | H | CH₃ |
| 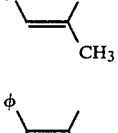 φ-cyclohexenyl | H | H | CH₂CH₃ |
| 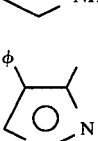 φ-CH=C(CH₃)- | H | H | CH₃ |
| 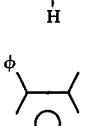 φ-pyrrolyl | H | H | CH₃ |
| 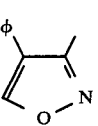 φ-pyrazolyl | H | H | CH₂CH₃ |
| 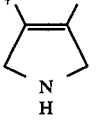 φ-imidazolyl | H | H | CH₃ |
| 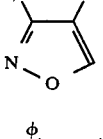 φ-isoxazolyl | H | H | CH₂CH₃ |
| 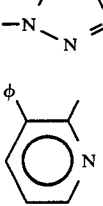 φ-pyrrolidinyl | H | H | CH₃ |
|  φ-isoxazolyl | H | H | CH₂CH₃ |
| φ-pyrazolyl | H | H | CH₃ |
| φ-pyridyl | H | —CH₂CH₂CH₂CH₂— | |

TABLE I-A-continued $$R_1-\overset{R_2}{\underset{\|}{C}}-NH-\overset{NR_3}{\underset{\|}{C}}-NR_4R_5$$

R₂ may be oxygen or sulfur

| R₁ | R₃ | R₄ R₅ |
|---|---|---|
| φ-(3-methyl-pyridin-2-yl) | H | —CH₂CH₂OCH₂CH₂— |
| φ-(3-methyl-pyridin-2-yl) | H | —CH₂CH₂CH₂CH₂CH₂— |
| φ-(3-methyl-pyridin-4-yl) | H | —CH₂CH₂CH₂CH₂— |
| φ-(3-methyl-pyrimidin-4-yl) | H | —CH₂CH₂OCH₂CH₂— |
| φ-(3-methyl-pyrimidin-4-yl) | H | —CH₂CH₂CH₂CH₂CH₂— |
| φ-(3-methyl-furan-2-yl) | H | —CH₂CH₂CH₂CH₂— |
| φ-(3-methyl-furan-2-yl) | H | —CH₂CH₂OCH₂CH₂— |
| φ-(3-methyl-furan-2-yl) | H | —CH₂CH₂CH₂CH₂CH₂— |
| φ-(3-methyl-thiophen-2-yl) | H | —CH₂CH₂CH₂CH₂— |
| φ-(3-methyl-thiophen-2-yl) | H | —CH₂CH₂OCH₂CH₂— |
| φ-(3-methyl-thiophen-2-yl) | H | —CH₂CH₂CH₂CH₂CH₂— |
| φ-(2-methyl-cyclopentenyl) | H | —CH₂CH₂CH₂CH₂— |
| φ-(2-methyl-cyclopentyl) | H | —CH₂CH₂OCH₂CH₂— |
| φ-(2-methyl-cyclohexyl) | H | —CH₂CH₂CH₂CH₂CH₂— |
| φ-CH=C(CH₃)— | H | —CH₂CH₂CH₂CH₂— |
| φ-(3-methyl-pyrrol-2-yl) | H | —CH₂CH₂CH₂CH₂— |
| φ-(3-methyl-pyrazol-4-yl) | H | —CH₂CH₂OCH₂CH₂— |
| φ-(3-methyl-imidazol-4-yl) | H | —CH₂CH₂CH₂CH₂CH₂— |
| φ-(3-methyl-isoxazol-4-yl) | H | —CH₂CH₂CH₂CH₂— |
| φ-(3-methyl-2,5-dihydro-pyrrol-4-yl) | H | —CH₂CH₂OCH₂CH₂— |
| φ-(4-methyl-isoxazol-3-yl) | H | —CH₂CH₂CH₂CH₂CH₂— |
| φ-(4-methyl-pyrazol-3-yl) | H | —CH₂CH₂CH₂CH₂— |

The acylguanidines of this invention may be readily converted to their nontoxic acid addition salts by customary methods in the art. The nontoxic salts of this invention are formed from acids which are pharmacologically acceptable in the intended dosages. Such salts include those prepared from inorganic acids and organic acids. Exemplary acids are hydrochloric acid, hydrobromic acid, sulfuric acid, nitric acid, phosphoric acid, methane sulfonic acid, benzene sulfonic acid, acetic acid, lactic acid, salicylic acid, benzoic acid, nicotinic acid, phthalic acid, stearic acid, oleic acid, abietic acid, and oxalic acid.

It is generally accepted in the pharmacological arts that nontoxic acid addition salts of pharmacologically active amine compounds do not differ in activities from their free base. The salts merely provide a convenient solubility factor.

A most preferred class of acyl guanidines for use in the anti-protozoal method of this invention are the compounds of Formula III.

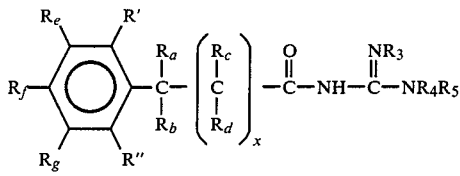

wherein:

x is zero or one;

$R_a$, $R_b$, $R_c$ and $R_d$ may be the same or different and are hydrogen, alkyl, alkoxy, hydroxy, amino, lower alkylamino, or either $R_a$ and $R_c$ or $R_b$ and $R_d$ form a double bond or together with the carbon atoms to which they are attached form a 5 or 6 membered heterocycle;

$R'$, $R''$, $R_e$, $R_f$, $R_g$, are hydrogen or phenyl substituents as defined herein and at least one of $R'$ and $R''$ is other than hydrogen;

$R_3$ and $R_4$ are hydrogen or lower alkyl;

$R_5$ is hydrogen, lower alkyl, lower alkenyl, lower alkynyl, lower alkanoyl, halo lower alkyl, and lower alkoxy.

The compounds described herein possess useful anti-protozoal properties as well as anticoccidial activity in mammalian and avian species.

PHARMACEUTICAL TESTING

Various tests in animals have been carried out to show the ability of the compounds of this invention to exhibit reactions that can be correlated with activity in humans. These tests involve such factors as the effect of the acyl guanidines on gastric secretion, their spasmolytic effect, their blood-pressure-lowering effect, their antiprotozoal effect and determination of their toxicity. It has been found that the compounds of this invention, when tested in the above variety of situations, show a marked activity.

One such test is the gastric secretion test. This test is carried out as follows: Shay rats are fasted for 4–8 hours and water is given ad lib. The rats are selected at random and separated into groups of ten. The animals are treated intraduodenally (I.D.) with the test compound or the vehicle immediately subsequent to the ligation of the stomach at the pyloric sphincter. The animals are sacrificed with chloroform at four hours post-drug-administration, the stomach removed and its contents assayed for volume, pH and total acids.

A second gastric secretion test is carried out on the dog. This outlined in the *Handbook of Physiology*, Section 6: Alimentary Canal, Volume II: Secretion; American Physiology Society, Washington, D.C., 1967.

To determine the anti-ulcer effectiveness, the following test is employed: Male Wistar rats (130–150 grams) are fasted for 24 hours, then given reserpine at 5 mg/kg i.p. Twenty-four hours later, the stomachs are removed and examined for ulceration. Ulcers are graded on a 0–4 scale and the number of ulcers is recorded. Pretreatment with the acyl guanidine compounds produces a decrease in ulcer grade and the number of ulcers compared to the control reserpine-treated rats.

Determination of antispasmolytic properties can be carried out by the procedure outlined by D. A. Brodie and S. K. Kundrats in their article entitled "Effect of Drugs on Gastric Emptying in Rats," *Fed. Proc.* 24:714 (1965). Acute toxicity is calculated according to the standard Litchfield-Wilcoxon procedure.

Various tests can be carried out in animal models to show the ability of the acyl guanidines of this invention to exhibit reactions that can be correlated with antidiarrheal activity in humans. The following test shows the ability of the compounds of this invention to inhibit diarrhea in animals and are known to correlate well with antidiarrheal activity in humans. Neimegeers, C. J. E. Lenaerts, F. M. and Janssen, P. A. J. Difenoxine, a potent, orally active and safe antidiarrheal agent in rats. *Arzneim-Forschung* (Drug. Res.) 22, 516–518, 1972.

Tests in animals can be carried out to show the ability of the compounds of this invention to inhibit reactions that can be correlated with antihypertensive effects in humans. One such test is outlined by Jacques de Champlain, Lawrence R. Krahoff and Julius Axelrod in *Circulation Research* XXIII:479 (1968). This testing method is known to correlate well with antihypertensive activity in humans and is a standard test used to determine antihypertensive properties.

Various tests can be carried out in animal models to show the ability of the acyl guanidines of this invention to exhibit reactions that can be correlated to anti-arrythmic properties and local anesthetic activity in humans.

Several different procedures generally employed in testing for local anesthetic activity are used to determine local anesthetic effects. These tests have been extensively used in the past and have given satisfactory results in defining the local anesthetic properties of compounds.

A discussion of experimental methods for evaluating local anesthetic properties of drugs is found in *Evaluation of Drug Activities: Pharmacometrics*, Vol. 1, Ed. by D. R. Lawrence and A. L. Bacharach, Academic Press, Inc. (London) Ltd. (1964). Applicants hereby incorporate by reference Chapter 9 of this book entitled "Local Anesthetics," pp. 204–214.

Various in vitro and in vivo tests can be carried out which show the anti-protozoal activity of the acyl guanidines of this invention. One in vitro test is described in L. R. McDougald and R. B. Galloway, "Eimeria tenella: Anticoccidial Drug Activity in Cell Cultures", Experimental Parasitology, 34, 189–196 (1973). In vivo test procedures are described in copending PCT Application No. PCT/US81/01142, filed Aug. 24, 1981, herein incorporated by reference. In view of the results of the aforesaid tests, the compounds of this invention possess antiprotozoal activity, and specifically anti-coccidial activity.

In in vitro tests using *Emimeria tenella*, a species of coccidiosis infecting poultry, the best activity is exhibited by compounds of formula I wherein $R_1$ is a phenacetyl group substituted in at least one or both ortho positions by halo or trihalo methyl groups and wherein $R_4$ is a lower alkyl group such as ethyl or n-propyl. For example, 1-(2,6-dichlorophenylacetyl)-3- ethyl guanidine possesses an optimum activity against *Eimeria tenella* in vitro at a concentration of 10 μg/ml, a toxicity of 100 μg/ml and a 50% lethal dose range between 82-135 mg/kg. Similar results were obtained with the 3-n-propyl homolog. In addition, excellent in vivo anticoccidial activity in chickens has been found with 1-(2,6-dichlorophenylacetyl)-3-ethyl guanidine.

The dosage regimen in carrying out the methods of this invention is that which ensures maximum therapeutic response until improvement is obtained, and thereafter the minimum effective level which gives relief. Thus, in general, the dosages are those that are therapeutically effective in the treatment of protozoal infections, of gastrointestinal disease conditions or symptoms, such as duodenal ulcer, peptic ulcer or diarrhea, and in the alleviation of hypertensive and arrhythmic disorders. The therapeutically effective doses correspond to those dosage amounts found effective in tests using animal models which are known to correlate to human activity for each particular disorder. In general, it is expected that daily doses between about 0.25 mg.kg and about 50 mg/kg (preferably in the range of 0.5-10 mg/kg/day) will be sufficient to produce the desired therapeutic effect, bearing in mind, of course, that in selecting the appropriate dosage in any specific case, consideration must be given to the patient's weight, general health, age, the severity of the disorder, and other factors which may influence response to the drug.

For all the above purposes, the acyl guanidines of this invention can be normally administered orally, parenterally or rectally. Orally, they may be administered as tablets, aqueous or oily suspensions, dispersible powders or granules, emulsions, hard or soft capsules, or syrups or elixirs. Parenterally, they may be administered as a salt in solution which pH is adjusted to physiologically accepted values. Aqueous solutions are preferred.

Compositions intended for oral use may be prepared according to any method known to the art for the manufacture of pharmaceutical compositions, and such compositions may contain one or more agents selected from the group consisting of sweetening agents, flavoring agents, coloring agents, and preserving agents, in order to provide a pharmaceutically administrable preparation.

Further, the active acyl guanidine may be administered alone or in admixture with other agents having the same or different pharmacological properties.

The composition may contain selected excipients, for example: inert diluents such as calcium carbonate, lactose, etc.; granulating and disintegrating agents such as maize starch, alginic acid, etc.; lubricating agents such as magnesium stearate, etc.; binding agents such as starch gelatin, etc.; suspending agents such as methylcellulose, vegetable oil, etc.; dispersing agents such as lecithin, etc.; thickening agents such as beeswax, hard paraffin, etc.; emulsifying agents such as naturally occurring gums, etc.; nonirritating excipients such as cocoa butter, polyethylene glycols, etc. Further, in formulating these compositions, for every 100 parts by weight of the composition, there may be present between 5 and 95 parts by weight of the active ingredient. The dosage unit form will generally contain between 0.1 mg and about 500 mg of the active ingredients of this invention. The preferred unit dose is between 1 mg and about 50 mg. The compositions may be taken 1-8 times daily, depending on the dosage unit required.

The following examples illustrate the preparation of tablets and capsules which constitute the preferred dosage forms for oral administration of the compounds of Formula I in accordance with the method of this invention as well as examples of sterile solutions for parenteral administration:

EXAMPLE A

A batch of homogeneous tablets was prepared, each having the following formula:

| Per Tablet | Ingredients | Per 1000 Tablets |
|---|---|---|
| 5 mg | 1-ethyl-3-(2,6-dichlorophenyl-acetyl) guanidine | 5 gm |
| 100 mg | Microcrystalline, Cellulose | 100 gm |
| 450 mg | Deionized water | 450 gm |
| 10 mg | Hydrogenated Castor Oil | 10 gm |
| 715 mg | | 715 gm |

The following procedure is used to prepare the tablets: 1-ethyl-3-(2,6-dichlorophenylacetyl) guanidine, cellulose and 100 gm of starch are blended together dry. A paste of the remaining starch is prepared with deionized water in a steamed jacketed pot. The two components are mixed, granulated and passed through a #S screen then dried in a Fluid Bed Dryer at about 400° C. and again passed through a #14 mesh screen. The composition is then formed into tablets by compressing on a Stokes Rotary Multi-Layer Tablet Press.

EXAMPLE B

Therapeutic compositions of the invention are prpared by using known techniques for compounding employing either the base or a salt as the active ingredient along with nontoxic excipients chosen in accordance with the particular form and properties desired for the therapeutic composition. Other therapeutic agents such as analgesics, tranquilizers, etc. may be added as desired.

1-propyl-3-(2,6-dichlorophenylacetyl)guanidine: 5 mg
tricalcium phosphate: 200 mg
talc: 50 mg
magnesium stearate: 10 mg
polyvinyl acetate: 40 mg In addition, there are protective excipients such as ethylcellulose, dibutylphthalate, propylene glycol, wax (white and/or carnauba), spermaceti, methylene chloride, and rectified diethyl ether. The ingredients are compressed to minimum size to provide a tablet of about 310 mg.

EXAMPLE C

A lot of 1,000 tablets each containing 10 mg of 1,1-dimethyl-3-(2,6-dichlorophenylacetyl) guanidine is prepared from the following types and amounts of ingredients:

1,1-dimethyl-3-(2,6-dichlorophenylacetyl)guanidine: 10 g
dicalcium phosphate: 1 kg
methylcellulose USP: 75 kg
talc: 150 g cornstarch: 200 g
magnesium stearate: 10 g The active ingredient and dicalcium phosphate are mixed thoroughly and granulated with a 7.5% solution of methylcellulose in water and passed through a #S screen and air-dried. The granules are passed through a #12 screen and combined with the talc, starch and magnesium stearate with thorough mixing after which the composition is compressed into tablets.

EXAMPLE D

A lot of 2-piece hard gelatin capsules, each containing 5 mg of 1-(4-chlorophenylacetyl)-3-methylguanidine are prepared from the following types and amounts of ingredients (the amounts given are per capsule):

1-(4-chlorophenylacetyl)-3-methylguanidine: 5 g
dicalcium phosphate: 500 g
talc: 150 g
magnesium stearate: 5 g The ingredients are mixed thoroughly and filled into capsules which are used for oral administration at the rate of about one every four hours. If desired, slow release forms can be provided or delayed release forms depending on choice of capsules and formulating ingredients.

By analogous methods and employing techniques known to the art, there are prepared formulations suitable for administration of an effective amount of any of the acyl guanidines of Formula I.

Additionally, animal feed compositions containing an antiprotozoal effective amount of a heterocyclic acyl guanidine of Formula III and a suitable feed carrier may be prepared according to methods known in the art.

We claim:

1. A method of treating coccidiosis in poultry comprising administering to poultry infected with coccidiosis a therapeutically effective amount of a compound of the formula

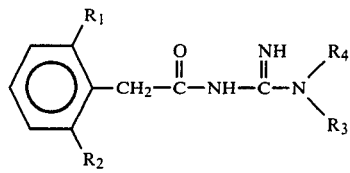

wherein:
$R_1$ and $R_2$ are hydrogen, halo, lower alkoxy, trihalomethyl, and at least one of $R_1$ and $R_2$ are halo or trihalomethyl;
$R_3$ is hydrogen or methyl; and
$R_4$ is lower alkyl; or a pharmaceutically acceptable salt thereof.

2. A method according to claim 1, wherein:
$R_1$ and $R_2$ are hydrogen or chloro;
$R_3$ is hydrogen; and
$R_4$ is methyl, ethyl, isopropyl, or n-propyl.

3. A method according to claim 1, wherein the compound is 1-ethyl-3-(2,6-dichlorophenylacetyl)-guanidine or a pharmaceutically acceptable salt thereof.

4. A method according to claim 1, wherein the compound is 1-propyl-3-(2,6-dichlorophenylacetyl)-guanidine or a pharmaceutically acceptable salt thereof.

5. A method according to claim 1, wherein the compound is 1,1-dimethyl-3-(2,6-dichlorophenylacetyl)-guanidine or a pharmaceutically acceptable salt thereof.

* * * * *